(12) United States Patent
Olsen et al.

(10) Patent No.: US 6,416,756 B1
(45) Date of Patent: Jul. 9, 2002

(54) MODIFIED PROTEASE HAVING 5 TO 13 COVALENTLY COUPLED POLYMERIC MOLECULES FOR SKIN CARE

(75) Inventors: Arne Agerlin Olsen, Virum; Annette Prento, Kdbakken, both of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/019,532

(22) Filed: Feb. 5, 1998

Related U.S. Application Data

(63) Continuation of application No. PCT/DK98/00015, filed on Jan. 12, 1998.
(60) Provisional application No. 60/051,831, filed on Jul. 7, 1997.

(30) Foreign Application Priority Data

Jan. 10, 1997 (DK) ................................. 0038/97
Jun. 25, 1997 (DK) ................................. 0754/97

(51) Int. Cl.[7] ........................ A61K 38/48; A61K 38/43; A61K 7/00; C12N 11/08; C12N 9/96
(52) U.S. Cl. .................. 424/94.63; 424/401; 424/94.1; 424/94.4; 424/94.6; 424/94.64; 424/94.65; 424/94.66; 424/94.67; 435/177; 435/180; 435/181
(58) Field of Search ................. 435/188, 174, 435/177, 180, 181; 424/94.1, 94.4, 94.6, 94.63, 401, 94.64, 94.65, 94.66, 94.67

(56) References Cited

U.S. PATENT DOCUMENTS 4,179,337 A   12/1979 Davis et al. ................ 435/181
5,597,720 A * 1/1997 Outtrup et al. ............. 435/221
5,622,850 A * 4/1997 Sloma et al. ................ 435/221

FOREIGN PATENT DOCUMENTS

| EP | 0 183 503 | 6/1986 |
| EP | 0 471 125 | 2/1992 |
| GB | 1183257 | 3/1970 |
| WO | WO 93/15189 | 8/1993 |
| WO | WO 96/17929 | 6/1996 |
| WO | WO 96/40792 | 12/1996 |
| WO | WO 97/30148 | 8/1997 |

* cited by examiner

Primary Examiner—David M. Naff
(74) Attorney, Agent, or Firm—Elias J. Lambiris

(57) ABSTRACT

Modified enzymes are prepared for use in skin care products by covalently coupling to the enzymes from 4 to 70 polymeric molecules with or without a linker such as a triazine ring. Molecular weight of the polymeric molecules may be from 1 to 35 kDa and of the enzymes from 15 to 100 kDa. The number and weight of polymeric molecules coupled is balanced with the weight and/or surface area of the enzymes. Enzymes include proteases such as subtilisins, lipases and oxidoreductases such as laccases and superoxide dismutase, and polymeric molecules include polysaccharides such as dextran or pullulan and polyalkylene oxides such as polyethylene glycol. The polymeric molecules may be coupled to the enzymes at the N-terminal amino group and/or lysine residues, and preferably at a position more than 5 Å from the active site of the enzymes. A preferred modified enzyme is a protease having from 5 to 13 coupled polymeric molecules. Skin care products containing the modified enzymes have improved stability and reduced allergenicity as compared to the products containing the unmodified enzymes.

17 Claims, 4 Drawing Sheets

MODIFIED PROTEASE HAVING 5 TO 13 COVALENTLY COUPLED POLYMERIC MOLECULES FOR SKIN CARE

CROSS-REFERENCE TO RELATED APPLICATIONS

This application is a continuation of PCT/DK98/00015 filed on Jan. 12, 1998, claims benefit of Provisional appln. Ser. No. 60/051,831 filed Jul. 7, 1997, and claims priority under 35 U.S.C. 119 of Danish application serial nos. 0038/97 and 0754/97 filed on Jan. 10, 1997 and Jun. 25, 1997, respectively, the contents of which are fully incorporated herein by reference.

FIELD OF THE INVENTION

The present invention relates to modified enzymes, a skin care composition comprising said modified enzyme and ingredients known to be used in skin care composition, a skin care product comprising a skin care composition of the invention and the use of said modified enzyme for improving the stability and/or for reducing the sensitization potential of enzyme.

BACKGROUND OF THE INVENTION

Since ancient time man has enjoyed taking baths and showers. This has not changed. For most people today bathing and showering are part of the daily rituals performed to maintain a good body hygiene and to obtain a pleasant scent. Certain people also regard a refreshing shower or bath in the morning as an important and necessary psychological experience without which they just cannot wake up.

A vast number of products for body care and maintenance of a good body hygiene, e.g. for cleansing and moisturising all parts of the body, are found on the consumer market. A few of these products comprise modified enzymes as an active ingredient.

Enzymes for Skin Care

The beneficial potential action of treating the skin with enzymes in the form of vegetables and fruits, such as cucumber, tomato, carrots, banana etc., have been known for a long period of time.

However, enzymes were not introduced into commercial skin care products before the 1970'ies, partly due to a limited knowledge about enzymes but also because enzymes were considered to have an unsatisfactory stability and also some disadvantageous properties in skin care products. For instance, cellulases were found to change the viscosity of lotions and creams containing carboxymethylcellulose; lipases resulted in changes in creams containing fatty acids esters; proteases were found to breakdown protein ingredients and to cause loss in viscosity.

Furthermore, also the high costs of enzymes at that time inhibited the application of enzymes in such personal care products.

The Human Skin

The human skin is composed of several layers. The top layer, the Epidermis, contains the fibrous protein keratin and functions as a sort of protective cover from the environment. The outer layer of the Epidermis is formed from organised cell death from the granular layer which lies underneath. In the granular layer numerous enzymes are released which convert the dead cell material to keratin.

The Corium (dermis) is connected to the Epidermis by way of the basal membrane and links the skin to the rest of the body through the circulatory system. The Corium is equipped with blood vessels, nerve fibres and lymphatic vessels and comprises a fibrous network of mainly collagen fibres with a limited amounts of elastin and reticulin fibres.

Modified Enzymes for Personal Care Products

As mentioned above some enzymes have an unsatisfactory stability and may under certain circumstances—dependent on the way of contact—cause an immune response, typically an IgG and/or IgE response.

It is today generally recognised that the stability of polypeptides are improved and the immune response are reduced when polypeptides, such as enzymes, are coupled to polymeric molecules.

Techniques for conjugating polymeric molecules to polypeptides are well known in the art.

One of the first suitable commercially techniques was described back in the early 1970'ies (U.S. Pat. No. 4,179,337). Said patent concerns non-immunogenic polypeptides, such as enzymes and peptide hormones coupled to polyethylene glycol (PEG) or polypropylene glycol. At least 15% of polypeptides' physiological activity is maintained.

GB patent no. 1,183,257 (Crook et al.) describes chemistry for conjugation of enzymes to polysaccharides via a triazine ring.

Further, techniques for maintaining of the enzymatic activities of enzyme-polymer conjugates are also known in the art.

WO 93/15189 (Veronese et al.) concerns a method for maintaining the activity in polyethylene glycol-modified proteolytic enzymes by linking the proteolytic enzyme to a macromolecularized inhibitor. The conjugates are intended for medical applications.

It has been found that the attachment of polypeptides to polymeric molecules in general has the effect of reducing the activity of the polypeptide or interfering with the interaction between the polypeptide and its substrate. EP 183 503 (Beecham Group PLC) discloses a development of the above concept by providing conjugates comprising pharmaceutically useful proteins linked to at least one water-soluble polymer by means of a reversible linking group.

EP 471,125 (Kanebo) discloses skin care products comprising a parent protease (the Bacillus protease Esperase®) coupled to polysaccharides through a triazine ring to improve the thermal and preservation stability. The coupling technique used is described in the above mentioned GB patent no. 1,183,257 (Crook et al.).

JP 3083908 describes a skin cosmetic material contains a transglutaminase from guinea pig liver modified with one or more water-soluble substance such as PEG, starch, cellulose etc. The modification is performed by activating the polymeric molecules and coupling them to the enzyme. The composition is claimed to be mild to the skin.

Short Summary of the General Knowledge Based on Prior Art

Techniques for coupling one or more polymeric molecules to a polypeptide molecule are known in the art. Further, it is known that such modified enzyme-polymer conjugates have a reduced immune response and have an improved stability.

SUMMARY OF THE INVENTION

It is the object of the present invention to provide improved modified enzyme conjugates suitable for use in skin care products.

The present inventors have found that when using modified enzyme with an activity suitable for skin care certain claims must be imposed on the enzyme and polymeric molecule to obtain improved stability and a reduced sensitisation potential while still having a substantial residual enzymatic activity maintained.

The inventors found that the number and weight of the polymeric molecules coupled to the surface of the enzyme must be balanced with the weight and/or surface area of the enzyme. Further, the position of coupling the polymeric molecules are also of importance.

In the first aspect the invention relates to a modified enzyme having from 4 to 70 polymeric molecules, with a molecule weight from 1 to 35 kDa, coupled covalently to the surface of parent enzymes having a molecule weight from 15 to 100 kDa.

In a case of the parent enzyme has a molecule weight from 15 to 35 kDa from 4 to 20 polymeric are coupled covalently should be coupled to the surface of the enzyme.

If the molecule weight of the parent enzyme is in the range from 35 to 60 kDa from 7 to 40, preferably 10 to 30 polymeric molecules are coupled to the surface of said parent enzyme.

Likewise, if the parent enzyme has a molecule weight from 60 to 80 kDa from 10 to 50, preferably 13 to 40 polymeric molecules are coupled to the surface of said parent enzyme.

From 15 to 70, preferably 18 to 60 polymeric molecules are coupled to the surface of parent enzymes having a molecule weight from 80 to 100 kDa.

Normally polymeric molecules are coupled to the amino groups ($-NH_2$) on the enzyme's surface and the N-terminal amino group. However, polymeric molecules may also be coupled to the carboxylic acid groups ($-COOH$) of amino acids in the enzyme chain positioned on the surface.

Preferred attachment groups are Lysine residues and the amino groups at the N-terminal.

Carboxylic acid attachment groups may be the carboxylic acid group of Aspartate or Glutamate and the C-terminal COOH-group.

The number of "attachment groups" in the present application also includes the number of the amino groups of Lysine residue in the polypeptide chain plus the N-terminal amino group.

The parent enzyme of the invention may be a hydrolase, including proteases, in particular subtilisins, or lipase, or an Oxidoreductase, including laccases and Superoxide dismutase.

In the second aspect the invention relates to skin care composition comprising a modified enzyme of the invention further ingredients being used in skin care products.

In the third aspect the invention relates to skin care product comprising a skin care composition of the invention.

The skin care product of the invention has improved stability and reduced sensitisation potential in comparison to corresponding skin care products (with parent enzymes).

The term "reduced sensitisation potential" means in the context of the present invention "reduced allergenicity" which means that the amount of produced IgE (in humans, and molecules with comparable effects in specific animals), which can lead to an allergic state, is decreased when inhaling a modified enzyme of the invention in comparison to the corresponding parent enzymes.

In the context of the present invention "skin care products" cover all personal care products used for cleansing, care and/or beautification of the skin of the body and further other products, such as hair care products, which during use might come in contact with the skin or respiratory system. Also corresponding products for animals are contemplated according to the present invention.

Specific examples of skin care products contemplated according to the present invention are soap, cosmetics, skin creams, skin gels, skin milk, skin lotion, cleansing cream, cleansing lotion, cleansing milk, cold cream, cream soap, makeup base, milky lotion, pack, calamine lotion, T zone essence, hand cream, essence powder, whitening powder, powder soap, cake soap, transparent soap, lip cream, lipstick, nourishing essence, creamy foundation, face powder, powder eye-shadow, powder foundation, nail polish remover, hair tonic, hair liquid, hair cream, hair gel, hair treatment, hair setting preparations, hair dyes, hair colorants, scalp treatment, shampoo, balsam, hair rinse, hair spray sun oil, sun screen, shaving foam and gel, shaving cream, baby oil, acne care products, antiperspirants, insect repellents, deodorants etc.

Assessment of Allergenicity

Assessment of allergenicity may be made by inhalation tests, comparing the effect of intratracheally (into the trachea) administrated parent enzymes with the corresponding modified enzymes according to the invention.

A number of in vivo animal models exist for assessment of the allegenicity of enzymes. Some of these models give a suitable basis for hazard assessment in man. Suitable models include a guinea pig model and a mouse model. These models seek to identify respiratory allergens as a function of elicitation reactions induced in previously sensitised animals. According to these models the alleged allergens are introduced intratracheally into the animals.

A suitable strain of guinea pigs, the Dunkin Hartley strain, do not as humans, produce IgE antibodies in connection with the allergic response. However, they produce another type of antibody the IgG1A and IgG1B (see e.g. Prentø, ATLA, 19, p. 8–14, 1991), which are responsible for their allergenic response to inhaled polypeptides including enzymes. Therefore, when using the Dunkin Hartley animal model, the relative amount of IgG1A and IgG1B is a measure of the allergenicity level.

A rat strain suitable for intratracheal exposure to polypeptides and enzymes is the Brown Norway strain. Brown Norway rats produce IgE as the allergic response.

The BALB/C mice strain is suitable for determining the IgE response caused by substcaneous injection.

More details on assessing respiratory allergens in guinea pigs and mice is described by Kimber et al.,(1996), Fundamental and Applied Toxicology, 33, pp. 1–10.

Other animals such as rats, rabbits etc. may also be used for comparable studies.

DETAILED DESCRIPTION OF THE INVENTION

Figure 1:
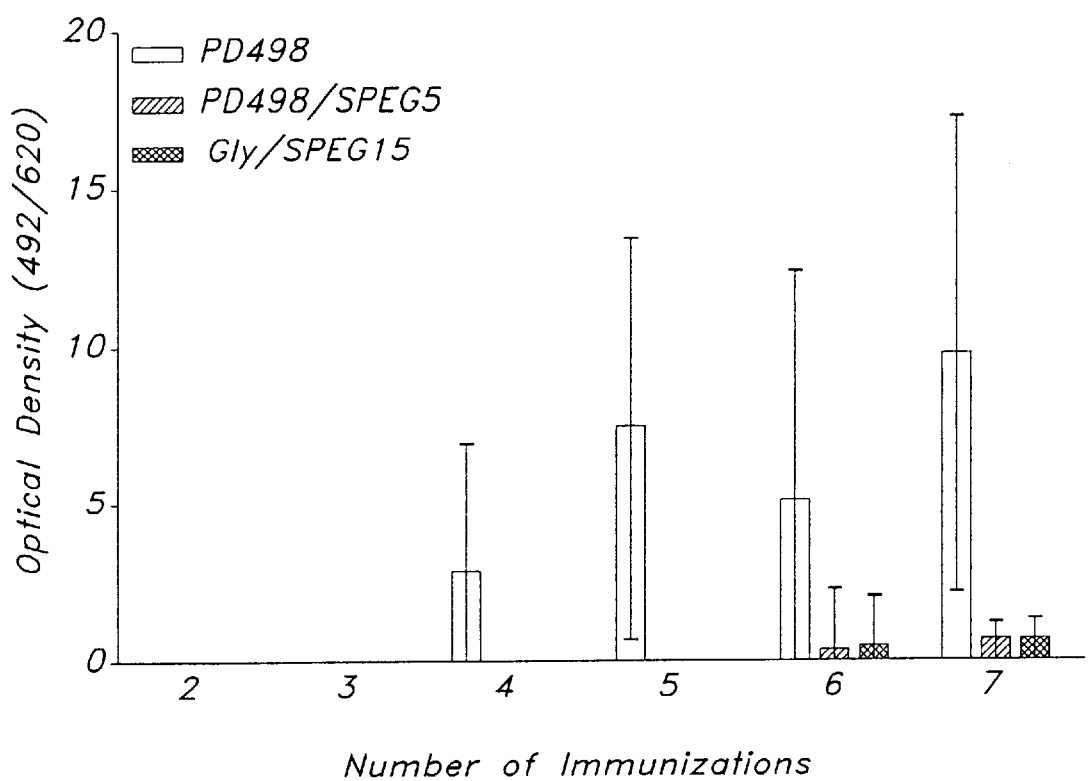
FIG. 1 shows the kinetics of the specific anti-PD498 IgE response in BALB/C mice after immunization with modified PD498-SPEG, unmodified PD498 and Glycine-SPEG 15,000.

It is the object of the present invention to provide modified enzymes suitable for skin care.

As mentioned above it is known to couple polymeric molecules to enzymes to improve the stability and to reduced the sensitisation potential of polypeptides, including enzymes. One of the problems arising when coupling polymeric molecules to enzymes are the loss of enzymatic activity.

According to the above mentioned EP 471,125 (Kanebo) a Bacillus protease Esperase® (available from Novo Nordisk A/S) is conjugated through a triazine ring with a 40 kDa dextran (Example 1) and a 50 kDa pullulan (Example 2).

Said Bacillus protease (i.e. Esperase®) has 3 accessible amino (—$NH_2$) attachment group to which polymeric molecules (in this case polysaccharides) may be coupled. The attachment groups are present as two amino groups (i.e. two Lysine residues on the surface of the 3D structure) and one N-terminal amino group. When coupling up to 3 polymeric molecules to said protease (a modification rate in the range of 68% to 71%, determined by the TNBS method (Haynes et al., (1967), Biochemistry 6, p. 641)) the residual enzymatic activity maintained is asserted to lie in the range from 45% (see Example 4) to 67% (see Example 3).

The present inventors have found that when using modified enzyme with an activity suitable for skin care certain claims must be imposed on the enzyme and polymeric molecule(s) to obtain improved stability and a reduced sensitisation potential while still having a substantial residual enzymatic activity maintained. The inventors found that the number and/or weight of the polymeric molecules coupled to the surface of the enzyme must be balanced with the weight and/or surface area of the enzyme. Further, the position (on the surface) of coupling the polymeric molecules are also of importance.

Enzyme Weight Versus the Number of Polymeric Molecules

The present invention is based on the general principle that the larger the surface area and/or the weight of the enzyme is the more polymeric molecules must be coupled to the surface of the enzyme to obtain improved stability, a substantial residual enzymatic activity and/or a reduced sensitisation potential.

If only few polymeric molecules are coupled to a heavy enzyme with a large surface area said few polymeric molecules are not capable of shielding (i.e. hiding/covering) the epitope(s) on the enzyme's surface responsible for the immune response resulting in the antibody formation, especially IgE antibodies.

The above mentioned EP 471,125 (Kanebo) describes coupling of few (i.e. up to 3) heavy (i.e. 40 and 50 kDa) polymeric molecules to the surface of the microbial protease Esperase® having a molecule weight of about 28 kDa.

In the first aspect the invention related to a modified enzyme suitable for skine care having from 4 to 70 polymeric molecules, with a molecule weight from 1 to 35 kDa, coupled covalently to the surface of a parent enzyme with a molecule weight from 15 to 100 kDa.

According to the present invention enzymes having a molecule weight of from 15 to 35 kDa, which is typical for many microbial enzymes, such bacterial proteases of e.g. Bacillus origin, are coupled covalently with from 4 to 20 polymeric molecules.

In other words, the modified enzyme may have 4, 5, 6, 7, 8, 9, 10, 11, 12, 13, 14, 15, 16, 17, 18, 19 or 20 polymeric molecules covalently coupled to the surface of 3D structure of the parent enzyme (including the N-terminal amino group).

According to the invention the preferred ratio between the weight and/or surface area of the enzyme, the number of coupled polymeric molecules and the weight of the polymer is displayed below in Table 1.

TABLE 1

| Molecule weight of enzyme ($M_w$) kDa | Number of polymeric molecules coupled to the enzyme | Average molecule weight of the polymeric molecules kDa |
| --- | --- | --- |
| 15 to 35 | 4–20 | 1–35 |
| 35 to 60 | 7–40 | 1–35 |
| 60 to 80 | 10–50 | 1–35 |
| 80 to 100 | 15–70 | 1–35 |
| more than 100 | more than 20 | 1–35 |

The molecule weight of the polymeric molecules may according to the invention be within the ranges between 1 and 35 kDa. However, if the polymeric molecules are to olight and/or too few the epitope(s) in question of the enzyme's surface may not be shielded sufficiently resulting in an immune response. The preferred molecule weight of the polymeric molecule lies according to the present invention between 4 to 25 kDa, especially 6 to 25 kDa, such as 8 to 20 kDa.

All polymer molecule weights mentioned are average molecule weights.

Position of the Coupled Polymeric Molecules

Virtually all ionized groups, such as the amino group of Lysine residues, are on the surface of the polypeptide molecule (see for instance Thomas E. Creighton, (1993), "Proteins", W.H. Freeman and Company, New York). Therefore, the number of readily accessible attachment groups (i.e. amino groups) on the enzyme's surface typically equals the number of Lysine residues in the primary structure of the enzyme plus the N-terminus amino group.

When choosing a parent enzyme for skin care compositions and products to be conjugated it is advantageous to use an enzyme with the number of attachment groups referred to above in Table 1.

Sensitisation Potential vs. Maintained Residual Enzymatic Activity

Especially for enzymes, in comparison with other proteins and polypeptides, there is a conflict between reducing the immune system's response toward enzymes and maintaining a substantial residual enzymatic activity as the activity of enzymes are connected with interaction between a substrate and the active site in a cleft in the enzyme structure.

According to the invention a "substantially" maintained residual activity means that more than 20%, 30% or 40%, better more than 50%, 60% or 70%, even better between 70% or 80%, up to between 80% and 90% and even up to 100%, of the activity of the enzyme is maintained.

Without being limited to any theory loss of enzymatic activity of modified enzymes might be a consequence of impeded access of the substrate to the active site in the form of spatial hindrance of the substrate by bulky/heavy polymeric molecules to the catalytic cleft of the enzyme. It might also, at least partly, be due to disadvantageous structural changes of the 3D structure of the enzyme. When coupling few bulky/heavy polymeric molecules to the enzyme surface it might cause uneven interactions on different parts of the enzyme molecule. This might lead to that the enzyme structure is pulled partly out of it normal configuration which in most cases will result in loss of enzymatic activity.

The modified protease described in EP 471,125 (Kanebo) has few (i.e. up to 3 polymeric molecules) heavy/bulky polymeric molecules (i.e. 40 and 50 kDa polysaccharides) coupled to amino groups on the enzyme's surface. The loss of enzymatic activity observed (i.e. 45% to 67% residual enzymatic activity) might be due to uneven interaction on different part of the enzyme's surface, causing the enzyme to be pulled out of it normal parent state configuration. Further, the bulky/heavy polymeric molecules coupled to the enzyme's surface might further impede the access of the substrate to the activity site of the enzyme resulting in the reduction of the maintained enzymatic activity.

When coupling a larger number of less bulky/heavy polymeric molecules to the enzyme surface the disadvantageous impact of the polymeric molecules is believed to be less pronounced, as the forces having affect on the enzyme structure are more evenly/uniformly distributed over a larger area on the surface of the enzyme. The impact of the polymeric molecules on the loss of activity are hereby less pronounced.

Consequently, it is preferred to couple more polymeric molecules (i.e. more than 4) with a relatively low molecule weight (i.e. 1–35 kDa) to the enzyme's surface (in the case of enzymes with a molecule weight from 15 to 35 kDa).

In a preferred embodiment of the invention the polymeric molecules are spread broadly over the surface of the enzyme, with the exception of the area close to the active site. In the present context "spread broadly" means positioned so that the polymeric molecules coupled to the attachment groups of the enzyme shield different parts of the enzyme surface, preferable the whole or close to the whole surface area away of the active site, to make sure that the relevant epitope(s) in question being recognisable are shielded and hereby not recognised by the immune system's antibodies. It is believed that the surface area of interaction between the enzyme and an antibody lies in the range about 500 $Å^2$ (26×19 Å) (see Sheriff et al. (1987), Proc. Natl. Acad. Sci. USA, Vol. 84, p. 8075).

Two or more attachment groups on the enzyme should preferably not lie close to each other as it will probably result in that only one polymeric molecule will be coupled.

To ensure a minimal loss of enzymatic activity it is preferred not to couple polymeric molecules in a close distance of the active site. The distance depends on the bulkiness of the polymeric molecules, as impeded access by the bulky polymeric molecules to the activity site is undesired. Therefore, the more bulky the polymeric molecules are the longer distance from the active site should the polymeric molecules be coupled.

Generally seen it is preferred that no polymeric molecules are attached within 5 Å, preferred 10 Å from the active site.

Further, enzymes having coupled polymeric molecules at (a) known epitope(s) recognisable by the immune system or close to said epitope are also considered advantageous according to the invention. If the position of the epitope(s) is(are) unknown it is advantageous to coupled as many polymeric molecules to the attachment groups available on the surface of the enzyme. It is preferred that said attachment groups are spread broadly over the surface of the enzyme in a suitable distance from the active site. Modified enzymes fulfilling the above claims to the distribution of coupled polymeric molecules on the surface of the enzyme are preferred according to the invention. Especially such enzymes having no or only very few polymeric molecules (i.e. 0 to 2) coupled within a distance of 0 to 5 Å, preferably 0 to 10 Å from the active site are preferred.

The Polymeric Molecule

The polymeric molecules coupled to the enzyme may be any suitable polymeric molecule, including natural and synthetic homo-polymers, such as polyols (i.e. poly-OH), polyamines (i.e. poly-$NH_2$) and polycarboxyl acids (i.e. poly-COOH), and further hetero-polymers i.e. polymers comprising one or more different coupling groups e.g. a hydroxyl group and amine groups.

Examples of suitable polymeric molecules include polymeric molecules selected from the group comprising polyalkylene oxides (PAO), such as polyalkylene glycols (PAG), including polyethylene glycols (PEG), methoxypolyethylene glycols (mPEG) and polypropylen glycols, PEG-glycidyl ethers (Epox-PEG), PEG-oxycarbonylimidazole (CDI-PEG), Branced PEGs, poly-vinyl alcohol (PVA), polycarboxylates, poly-(vinylpyrolidone), poly-D,L-amino acids, polyethylene-co-maleic acid anhydride, polystyrene-co-malic acid anhydrid, dextrans including carboxymethyl-dextrans, heparin, homologous albumin, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-straches and hydroxy propyl-starches, glycogen, agaroses and derivates thereof, guar gum, pullulan, inulin, xanthan gum, carrageenin, pectin, alginic acid hydrolysates and bio-polymers.

Preferred polymeric molecules are non-toxic polymeric molecules such as (m)polyethylene glycol ((m)PEG) which further requires a relatively simple chemistry for its covalently coupling to attachment groups on the enzyme's surface.

Generally seen polyalkylene oxides (PAO), such as polyethylene oxides, such as PEG and especially MPEG, are the preferred polymeric molecules, as these polymeric molecules, in comparison to polysaccharides such as dextran, pullulan and the like, have few reactive groups capable of cross-linking.

Even though all of the above mentioned polymeric molecules may be used according to the invention the methoxypolyethylene glycols (mPEG) may advantageously be used. This arise from the fact that methoxyethylene glycols have only one reactive end capable of conjugating with the enzyme. Consequently, the risk of cross-linking is less pronounced. Further, it makes the product more homogeneous and the reaction of the polymeric molecules with the enzyme easier to control.

Activation of Polymers

If the polymeric molecules to be conjugated with the enzyme are not active it must be activated by the use of a suitable method. The polymeric molecules may be coupled to the enzyme through a linker. Suitable linkers are well known to the skilled person.

Methods and chemistry for activation of polymeric molecules as well as for conjugation of proteins are intensively described in the literature. Commonly used methods for activation of insoluble polymers include activation of functional groups with cyanogen bromide, periodate, glutaraldehyde, biepoxides, epichlorohydrin, divinylsulfone, carbodiimide, sulfonyl halides, trichlorotriazine etc. (see R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). Some of the methods concern activation of insoluble polymers but are also applicable to activation of soluble polymers e.g. periodate, trichlorotriazine, sulfonylhalides, divinylsulfone, carbodiimide etc. The functional groups being amino, hydroxyl, thiol, carboxyl, aldehyde or sulfydryl on the polymer and the chosen attachment group on the protein must be considered in choosing the activation and conjugation chemistry which normally consist of i) activation of polymer, ii) conjugation, and iii) blocking of residual active groups.

In the following a number of suitable polymer activation methods will be described shortly. However, it is to be understood that also other methods may be used.

Coupling polymeric molecules to the free acid groups of enzymes can be performed with the aid of diimide and for example amino-PEG or hydrazino-PEG (Pollak et al., (1976), J. Amr. Chem. Soc., 98, 289–291) or diazoacetate/amide (Wong et al., (1992), "Chemistry of Protein Conjugation and Crosslinking", CRC Press).

Coupling polymeric molecules to hydroxy groups are generally very difficult as it must be performed in water. Usually hydrolysis predominates over reaction with hydroxyl groups.

Coupling polymeric molecules to free sulfhydryl groups can be reached with special groups like maleimido or the ortho-pyridyl disulfide. Also vinylsulfone (U.S. Pat. No. 5,414,135, (1995), Snow et al.) has a preference for sulfhydryl groups but is not as selective as the other mentioned.

Accessible Arginine residues in the polypeptide chain may be targeted by groups comprising two vicinal carbonyl groups.

Techniques involving coupling electrophilically activated PEGs to the amino groups of Lysines are also be useful. Many of the usual leaving groups for alcohols give rise to an amine linkage. For instance, alkyl sulfonates, such as tresylates (Nilsson et al., (1984), Methods in Enzymology vol. 104, Jacoby, W. B., Ed., Academic Press: Orlando, p. 56–66; Nilsson et al., (1987), Methods in Enzymology vol. 135; Mosbach, K., Ed.; Academic Press: Orlando, pp. 65–79; Scouten et al., (1987), Methods in Enzymology vol. 135, Mosbach, K., Ed., Academic Press: Orlando, 1987; pp 79–84; Crossland et al., (1971), J. Amr. Chem. Soc. 1971, 93, pp. 4217–4219), mesylates (Harris, (1985), supra; Harris et al., (1984), J. Polym. Sci. Polym. Chem. Ed. 22, pp 341–352), aryl sulfonates like tosylates, and para-nitrobenzene sulfonates can be used.

Organic sulfonyl chlorides, e.g. Tresyl chloride, effectively converts hydroxy groups in a number of polymers, e.g. PEG, into good leaving groups (sulfonates) that, when reacted with nucleophiles like amino groups in polypeptides allow stable linkages to be formed between polymer and polypeptide. In addition to high conjugation yields, the reaction conditions are in general mild (neutral or slightly alkaline pH, to avoid denaturation and little or no disruption of activity), and satisfy the non-destructive requirements to the polypeptide.

Tosylate is more reactive than the mesylate but also more unstable decomposing into PEG, dioxane, and sulfonic acid (Zalipsky, (1995), Bioconjugate Chem., 6, 150–165). Epoxides may also been used for creating amine bonds but are much less reactive than the above mentioned groups.

Converting PEG into a chloroformate with phosgene gives rise to carbamate linkages to Lysines. This theme can be played in many variants substituting the chlorine with N-hydroxy succinimide (U.S. Pat. No. 5,122,614, (1992); Zalipsky et al., (1992), Biotechnol. Appl. Biochem., 15, p. 100–114; Monfardini et al., (1995), Bioconjugate Chem., 6, 62–69, with imidazole (Allen et al., (1991), Carbohydr. Res., 213, pp 309–319), with para-nitrophenol, DMAP (EP 632 082 A1, (1993), Looze, Y.) etc. The derivatives are usually made by reacting the chloroformate with the desired leaving group. All these groups give rise to carbamate linkages to the peptide.

Furthermore, isocyanates and isothiocyanates may be employed yielding ureas and thioureas, respectively.

Amides may be obtained from PEG acids using the same leaving groups as mentioned above and cyclic imid thrones (U.S. Pat. No. 5,349,001, (1994), Greenwald et al.). The reactivity of these compounds are very high but may make the hydrolysis to fast.

PEG succinate made from reaction with succinic anhydride can also be used. The hereby comprised ester group make the conjugate much more susceptible to hydrolysis (U.S. Pat. No. 5,122,614, (1992), Zalipsky). This group may be activated with N-hydroxy succinimide.

Furthermore, a special linker can be introduced. The oldest being cyanuric chloride (Abuchowski et al., (1977), J. Biol. Chem., 252, 3578–3581; U.S. Pat. No. 4,179,337, (1979), Davis et al.; Shafer et al., (1986), J. Polym. Sci. Polym. Chem. Ed., 24, 375–378.

Coupling of PEG to an aromatic amine followed by diazotation yields a very reactive diazonium salt which in situ can be reacted with a peptide. An amide linkage may also be obtained by reacting an azlactone derivative of PEG (U.S. Pat. No. 5,321,095, (1994), Greenwald, R. B.) thus introducing an additional amide linkage.

As some peptides do not comprise many Lysines it may be advantageous to attach more than one PEG to the same Lysine. This can be done e.g. by the use of 1,3-diamino-2-propanol.

PEGs may also be attached to the amino-groups of the enzyme with carbamate linkages (WO 95/11924, Greenwald et al.). Lysine residues may also be used as the backbone.

The Parent Enzyme

The conjugates of the invention described above may be prepared on the basis of selected parent enzymes using any suitable technique known in the art.

The term "parent" enzyme is intended to indicate any uncoupled enzyme (i.e. an enzyme to be modified). The enzyme may preferably be of microbial origin, such as bacterial, filamentous fungus or yeast origin.

The parent enzyme may be a naturally-occurring (or wild-type) enzyme or may be a variant thereof.

Assessing/Selecting Suitable Parent Enzyme

The 3-dimensional structure of the enzyme is of interest in connection with assessing/selecting suitable parent enzymes to be modified. The 3-dimentional structure may be an X-ray structure, an NMR structure or a model-built structure. The Brookhaven Databank may be the source of X-ray and NMR-structures.

A model-built structure may be produced by the person skilled in the art if one or more 3D-structure(s) exist(s) of homologous enzyme (s) sharing at least 30% sequence identity with the enzyme in question. Several software packages, such as the "Homology 95.0" package from Biosym, exist which may be employed to construct a model structure.

Typical actions required for the construction of a model structure are: alignment of homologous sequences for which 3D-structures exist, definition of Structurally Conserved Regions (SCRs), assignment of coordinates to SCRs, search for structural fragments/loops in structure databases to replace Variable Regions, assignment of coordinates to these regions, and structural refinement by energy minimization. Regions containing large inserts ($\geq$3 residues) relative to the known 3D-structures are known to be quite difficult to model, and structural predictions must be considered with care.

Having obtained the 3D-structure of the enzyme in question, or a model of the structure based on homology to known structures, this structure serves as an essential prerequisite for the identifying suitable parent enzymes which when modified has a reduced allergenicity and a substantially maintained residual enzymatic activity.

Preferred enzymes for skin care products are enzymes having a substantially enzymatic activity in the pH range used in the skin care product.

The Enzyme Activity

The parent enzyme may have any activity known to be used for skin care. Contemplated enzymes including Oxidoreductases (E.C. 1, "Enzyme Nomenclature, (1992), Academic Press, Inc.), such as laccase and Superoxide dismutase (SOD); Hydrolases E.C. 3, including proteases, especially subtilisins, and lipolytic enzymes; Transferases, (E.C. 2), such as transglutaminases (TGases); Isomerases (E.C. 5), such as Protein disulfide Isomerases (PDI).

Hydrolases

Proteolytic Enzymes

Contemplated proteolytic enzymes includes selected from the group of acidic aspartic proteases, cysteine proteases, serine proteases, such as subtilisins, or metallo proteases, with the above indicated properties (i.e. number of attachment groups, position of attachment groups etc.).

Specific examples of suitable parent proteases having a suitable number of attachment groups are indicated in Table 2 below:

TABLE 2

| Enzyme | Number of attachment groups | Molecule weight kDa | Reference |
| --- | --- | --- | --- |
| PD498 | 13 | 29 | Seq. ID No. 2 (WO 93/24623) |
| Savinase ® | 6 | 27 | von der Osten et al., (1993), Journal of Biotechnology, 28, p. 55+ |
| Proteinase K | 9 | 29 | Gunkel et al., (1989), Eur. J. Biochem, 179, p. 185–194 |
| Proteinase R | 5 | 29 | Samal et al, (1990), Mol. Microbiol, 4, p. 1789–1792 |
| Proteinase T | 14 | 29 | Samal et al., (1989), Gene, 85, p. 329–333 |
| Subtilisin DY | 13 | 27 | Betzel et al. (1993), Arch. Biophys, 302, no. 2, p. 499–502 |
| Lion Y | 15 | 46 | SEQ ID NO. 4 (JP 04197182-A) |
| Rennilase ® | | 39 | Available from Novo Nordisk A/S |
| Ja16 | 5 | 28 | WO 92/17576 |
| Thermolysin | 12 | 34 | Titani et al., (1972) Nature New Biol. 238, p. 35–37, and SEQ ID NO 5 |
| Alcalase ® (a natural subtilisin Carlberg variant) | 10 | 27 | von der Osten et al., (1993), Journal of Biotechnology, 28, p. 55+ |

The subtilisin PD498 has a molecule weight of 29 kDa and is shown in SEQ ID NO. 2. PD498 has 12 Lysine groups for attachment on the surface of the enzyme plus one N-terminal amino group. As mentioned above preferred enzyme has Lysine spread broadly over the enzyme's surface. PD498 has no Lysine residues in a distance of 0–10 Å from the active site which makes it especially suitable in modified form. Further, the Lysine residues are spread broadly on the surface of the enzyme (i.e. away from the active site).

The enzyme Subtilisin DY has a molecule weight of 27 kDa and has 12 amino groups (i.e. Lysine residues) on the surface of the enzyme and one N-terminal amino group (see SEQ ID NO. 3).

The parent protease Lion Y has a molecule weight of 46 kDa and has 14 amino groups (i.e. Lysine residues) on the surface of the enzyme plus one N-terminal amino group (see SEQ ID NO. 4).

The neutral metallo protease Thermolysin has a molecule weight of 34 kDa and has 11 amino groups (i.e. Lysine residues) on the surface plus one N-terminal amino group. (See SEQ ID NO 5).

Lipolytic Enzymes

Contemplated lipolytic enzymes include *Humicola lanuginosa* lipases, e.g. the one described in EP 258 068 and EP 305 216, *Humicola insolens,* lipase a *Rhizomucor miehei* lipase, e.g. as described in EP 238 023, Absidia sp. lipolytic enzymes (WO 96/13578), a Candida lipase, such as a *C. antarctica* lipase, e.g. the *C. antarctica* lipase A or B described in EP 214 761, a Pseudomonas lipase such as a *P. alcaligenes* and *P. pseudoalcaligenes* lipase, e.g. as described in EP 218 272, a *P. cepacia* lipase, e.g. as described in EP 331 376, a Pseudomonas sp. lipase as disclosed in WO 95/14783, a Bacillus lipase, e.g. a *B. subtilis* lipase (Dartois et al., (1993) Biochemica et Biophysica acta 1131, 253–260), a *B. stearothermophilus* lipase (JP 64/744992) and a *B. pumilus* lipase (WO 91/16422). Other types of lipolytic include cutinases, e.g. derived from *Pseudomonas mendocina* as described in WO 88/09367, or a cutinase derived from *Fusarium solani pisi* (e.g. described in WO 90/09446).

Oxidoreductases

Laccases

Contemplated laccases include the laccases disclosed in WO 96/00290 and WO 95/33836 from Novo Nordisk.

Transferases

Transglutaminases

Suitable transferases include any transgluteminases disclosed in WO 96/06931 (Novo Nordisk A/S) and WO 96/22366 (Novo Nordisk A/S).

Isomerases

Protein Disulfide Isomerase

Without being limited thereto suitable protein disulfide isomerases include PDIs described in WO 95/01425 (Novo Nordisk A/S).

Enzyme Activities Suitable for Skin Care

In the second aspect the invention relates to skin care compositions comprising a modified enzyme of the invention and ingredients known to be used in skin care compositions A number of enzyme activities are known to be used skin care compositions.

Proteases

Proteases are effective ingredients in skin cleaning products. Proteases remove the upper layer of dead keratinous skin cells and thereby makes the skin look brighter and more fresh. Further, proteases also improves the smoothness of the skin.

Proteases are used in toiletries, bath and shower products, including shampoos, conditioners, lotions, creams, soap bars, toilet soaps, and liquid soaps.

Lipases

Lipases can be applied for cosmetic use as active ingredients in skin cleaning products and anti-acne products for removal of excessive skin lipids, and in bath and shower products such as creams and lotions as active ingredients for skin care.

Lipases can also be used in hair cleaning products (e.g. shampoos) for effective removal of sebum and other fatty material from the surface of hair.

Oxidoreductases

The most common oxidoreductase for personal care purposes is an oxidase (usually glucose oxidase) with substrate (e.g. glucose) that ensures production of $H_2O_2$, which then will initiate the oxidation of for instance $SCN^-$ or $I^-$ into anti-microbial reagents (SCNO⁻ or $I_2$) by a peroxidase (usually lactoperoxidase). This enzymatic complex is known in nature from e.g. milk and saliva.

It is being utilised commercially as anti-microbial system in oral care products (mouth rinse, dentifrice, chewing gum) where it also can be combined with an amyloglucosidase to produce the glucose. These systems are also known in cosmetic products for preservation.

Another application of oxidoreductases are oxidative hair dyeing using oxidases, peroxidases and laccases (See e.g. WO 96/00290 or WO 95/33836 from Novo Nordisk).

Free radicals formed on the surface of the skin (and hair) known to be associated with the ageing process of the skin (spoilage of the hair).

The free radicals activate chain reactions that leads to destruction of fatty membranes, collagen, and cells.

The application of free radical scavengers such as Superoxide dismutase into cosmetics is well-known (R. L. Goldemberg, DCI, November 93, p. 48–52).

Protein disulfide isomerase (PDI) is also an oxidoreductase. It may be utilised for waving of hair (reduction and reoxidation of disulfide bonds in hair) and repair of spoiled hair (where the damage is mainly reduction of existing disulfide bonds).

Transglutaminase

Skin care compositions for application to human skin, hair or nails comprise (a) an amino-functional active ingredient, (b) transglutaminase to catalyse crosslinking of the active ingredient to the skin, hair or nails, and (c) a carrier is known from U.S. Pat. No. 5,490,980.

A cosmetic composition suitable for application to mammalian skin, hair or nails comprising: (a) at least one corneocyte envelope protein in an amount sufficient to provide a protective layer on said skin, hair or nails; (b) a transglutaminase in an amount sufficient to form covalent bonds between the corneocyte envelope protein and externally exposed corneocyte proteins present in the stratum corneum of said skin, hair or nails; (c) calcium ions in an amount sufficient to activate the transglutaminase; and (d) a cosmetically acceptable vehicle, wherein the composition comprises an emulsion having two phases and wherein the corneocyte envelope protein is contained in one of the phases and the transglutaminase is contained within the other phase (see U.S. Pat. No. 5,525,336).

JP 3083908 describes a skin cosmetic material contains a transglutaminase modified with a water-soluble substance. The modifying substance is, e.g., one or more of polyethylene glycol, ethylene glycol, propylene glycol, glycerine, polyvinyl alcohol, glucose, sucrose, alginil acid, carboxymethyl cellulose, starch, and hydroxypropyl cellulose. The modification is done, e.g., by introducing reactive groups and bonding to the enzyme. For providing a material mild to the skin, causing less time-lapse discolouring and odorising, and having good effects of curing rough skin, retaining moisture, and conditioning the skin beautifully.

The Skin Care Products of the Invention

In the third aspect the invention relates to a skin care product comprising a skin care composition of the invention. The term "skin care products" are defined above.

A skin care product of the invention may comprise from an effective amount of modified enzymes of the invention. Such effective amounts known to the skilled person may will often lie in the range from above 0 to 5% of the final skin care product.

Contemplated skin care products of the invention include, without being limited thereto, the following products: soap, cosmetics, skin creams, skin milk, skin lotion, skin gel, cleansing cream, cleansing lotion, cleansing milk, cold cream, cream soap, makeup base, milky lotion, pack, calamine lotion, T zone essence, hand cream, essence powder, whitening powder, powder soap, cake soap, transparent soap, lip cream, lipstick, nourishing essence, creamy foundation, face powder, powder eye-shadow, powder foundation, nail polish remover, hair tonic, hair liquid, hair cream, hair gel, hair treatment, hair setting preparations, hair dyes, hair colorants, scalp treatment, shampoo, balsam, hair rinse, hair spray sun oil, sun screen, shaving foam, shaving cream, baby oil, acne care products, antiperspirants, insect repellents, deodorants etc.

General Skin Care Product Formulations

The term "ingredients used in skin care products" is meant to cover all ingredients which are known to be used in skin care product formulations. Examples of such ingredients ingredients can be found in "Cosmetics and Toiletries" edited by Wilfried Umbach and published by Ellis Horwood, Limited, England, (1991), and "Surfactants in Consumer Products", edited by J. Falbe and published by Spring-Verlag, (1987).

In the following a non exhausting list of guide formulations are listed. These provide an overwiev of formulations of important skin care products contemplated according to the invention.

| Ingredients | Examples | |
|---|---|---|
| Toilet soap | | |
| | | % |
| Surfactants | Soap (sodium salt) | 83–87 |
| Sequestering agents | Ethylenediamine tetraacetate | 0.1–0.3 |
| Consistency regulators | Sodium chloride | approx. 0.5 |
| Dyestuffs | | <0.1 |
| Optical brighteners | | <0.1 |
| Antioxidants | 2,6-bis(1,1-Dimethylethyl)-4-methyl phenol(BHT) | 0.1–0.3 |
| Whitening agents | Titanium dioxide | 0.1–0.3 |
| Fragrances | | 1.0–2.0 |
| Enzymes | Protease/Lipase | 0–5 |
| Water | | Balance |
| Syndet (Synthetic Detergents) | | |
| | | % |
| Surfactants | Lauryl sulfate | 30–50 |
| | Lauryl sulfo succinate | 1–12 |
| Refatting agents | Fatty alcohols | 10–20 |
| Plasticizers | Stearyl mono/diglycerides | 0–10 |
| Fillers | Starches | 0–10 |
| Active agents | Salicylic acid | 0–1 |
| Dyestuffs | | <0.2 |
| Fragrances | | 0–2 |
| Enzymes | Protease/Lipase | 0–5 |
| Water | | Balance |
| Foam bath and shower bath | | |
| | | % Foam bath / % Shower bath |
| Surfactants | Lauryl ether sulfate | 10–20 / 10–12 |
| | Coco amidopropyl dimethyl betaine | 2–4 / 2–4 |
| | Ethoxylated fatty acids | 0.5–2 / — |
| Refatting agents | Fatty alcohols | 0.5–3 |
| | Ethoxylated fatty alcohols | 0.5–5 / 0–4 |

-continued

| Ingredients | Examples | | |
|---|---|---|---|
| | | % Foam bath | % Shower bath |
| Enzymes | Protease/Lipase | 0–5 | 0–5 |
| Foam stabilizers | Fatty acid alkanol amides | 0.2–2 | 0–4 |
| Conditioners | Quaternized hydroxypropyl cellulose | — | 0–0.5 |
| Thickeners | Sodium chloride | 0–3 | 0–3 |
| Pearlescent agents | Ethyleneglycol stearate | 0–2 | — |
| Active agents | Vegetable extracts | 0–1 | 0–1 |
| Preservatives | 5-Bromo-5-nitro-1,3-dioxane | 0.1 | 0.1 |
| Dyestuffs | | 0.1–0.2 | 0.1 |
| Fragrances | | 0.3–3 | 0.3–2 |
| Enzymes | Protease/Lipase | 0–5 | 0–5 |
| Water | | Balance | Balance |

Skin cream (water-in-oil type and oil-in-water type)

| | | % Water-in-oil type | % Oil-in-water type |
|---|---|---|---|
| Emulsifiers | Sorbitane sesquioleate | 3–5 | — |
| | Aluminum stearate | 1–2 | — |
| | Triethanolamine stearate | — | 1–2 |
| | Cetyl/Stearyl alcohol polyglycol ethers | — | 1–3 |
| Fatty derivatives | Isopropyl palmitate | 1–5 | 0–3 |
| | Cetyl/Stearyl alcohol | — | 0–2 |
| | 2-Octyl dodecanol | 2–10 | 3–7 |
| | Stearic/Palmitic acid | — | 0–3 |
| | Caprylic/Capric acid triglycerides | 5–10 | — |
| | Glycerine stearate | — | 0–5 |
| Moisturizers | Glycerine | 1–5 | 1–5 |
| | Sorbitol | 1–5 | 1–5 |
| | Poly (hydroxy carboxylic acids) | 0.5–2 | — |
| | Propyleneglycol | — | 0–3 |
| Stabilizers | Magnesium sulfate | 0–0.8 | — |
| Preservatives | p-Hydroxy benzoic acid ester | 0.2–0.4 | 0.2–0.4 |
| Enzymes | Protease/Lipase | 0–5 | 0–5 |
| Water | | Balance | Balance |

Body lotion (oil-in-water type) and skin lotion for application on the wet skin

| | | % Body lotion | % Skin lotion |
|---|---|---|---|
| Emulsifiers | Cetyl/Stearyl alcohol polyglycol ethers | 1–3 | — |
| | Sorbitane monolaurate | 0.5–1 | — |
| | Sodium stearate | — | 1–2 |
| | Sodium lauryl ether sulfate | — | 0.5–2 |
| Fatty derivatives | 2-Octyl dodecanol | 1–3 | 0–5 |
| | Paraffin oils | — | 20–25 |
| | Bees wax | 0.5–1 | — |
| | Isooctyl stearate | 3–7 | — |
| | Isopropyl palmitate | — | 2–5 |
| Moisturizers | Glycerine | 3–5 | 5–10 |
| | Sorbitol | — | 0–5 |
| Thickeners | Polyacrylates | 0–0.3 | 0–1 |
| | Methyl hydroxypropyl cellulose | 0–0.3 | 0–0.5 |
| Preservatives | p-Hydroxy benzoic acid ester | 0.2–0.4 | 0.2–0.4 |
| Enzymes | Protease/Lipase | 0–5 | 0–5 |
| Water | | Balance | Balance |

-continued

| Ingredients | Examples | |
|---|---|---|
| | Face lotion | |
| | | % |
| Surfactants | Magnesium lauryl ether sulfate | 0.2–0.5 |
| Refatting agents | Di-n-butyl adipate | 1–2 |
| Solubilizers | Castor oil polyglycol ethers | 0.1–1 |
| Cleaning and refreshing components | Ethanol | 0–15 |
| Moisturizers | Glycerine | 0–5 |
| | Sorbitol | 0–5 |
| Preservatives | p-Hydroxy benzoic acid ester | 0.2–0.4 |
| Adstringents | Vegetable extracts | 1–5 |
| Antiirritants | Panthenol | 0–1 |
| | Allantoine | 0–0.2 |
| | Vegetable extracts | 0.5–3 |
| Enzymes | Protease/Lipase | 0–5 |
| Water | | Balance |

Hair shampoo

| | | % |
|---|---|---|
| Surfactants | Lauryl ether sulfate | 12–16 |
| | Coco fatty acid amidopropyl dimethyl betaine | 2–5 |
| | Fatty acid polyglycol esters | 0–2 |
| Foam boosters | Fatty acid ethanol amides | 0.5–2.5 |
| Conditioners | Quaternized hydroxyethyl cellulose | 0.4–1 |
| | Protein hydrolysates | 0.2–1 |
| Refatting agents | Ethoxylated lanolin alcohols | 0.2–1 |
| Additives | Anti-dandruff agents | 0–1 |
| Preservatives | 5-Bromo-5-nitro-1,3-dioxane | 0.1–0.3 |
| Pearlescent agents | Ethyleneglycol stearate | 0–2 |
| Dyestuffs | | <0.1 |
| pH-Regulators | Acids/Bases | 0.1–1 |
| Fragrances | | 0.3–0.5 |
| Enzymes | Protease/Lipase | 0–5 |
| Water | | Balance |

Hair rinse and hair conditioner

| | | % Hair rinse | % Hair conditioner |
|---|---|---|---|
| Surfactants | Fatty alcohol polyglycol ethers | 0.1–0.2 | 1.5–2.5 |
| | Cetyl trimethyl ammonium chloride | 0.5–1 | — |
| | Dimethyl benzyl stearyl ammonium chloride | — | 0.5–1 |
| Refatting agents | Cetyl/Stearyl mono/diglyceride | 0.5–1.5 | 1.5–2.5 |
| Consistency regulators | Fatty alcohols | 1–2.5 | 2.5–3.5 |
| Thickeners | Methyl hydroxypropyl cellulose | 0.3–0.6 | 0.4–0.8 |
| Conditioners | Quaternized hydroxyethyl cellulose | 0.1–0.3 | 0.3–0.4 |
| Preservatives | p-Hydroxy benzoic acid ester | 0.1–0.3 | 0.1–0.3 |
| Dyestuffs | | <0.1 | <0.1 |
| pH-Regulators | Acids/Bases | 0.1–1 | 0.1–1 |
| Fragrances | | 0.2–0.5 | 0.2–0.5 |
| Enzymes | Protease/Lipase | 0–5 | 0–5 |
| Water | | Balance | Balance |

Hair dyes

| | | % |
|---|---|---|
| Component 1: | Alkaline dyeing cream | |
| Surfactants | Lauryl ether sulfate | 1–4 |

-continued

| Ingredients | Examples | |
|---|---|---|
| Consistency | Ethoxylated castor oil | 1–2 |
| | Fatty alcohols | 8–10 |
| Reductants | Sodium sulfite | 0.8–1.2 |
| Buffers | Ammonium chloride | 0.5–1 |
| Sequestrants | 1-Hydroxyethane-1,1-diphosphonic acid | 0.1–0.2 |
| Alkaline agents | Ammonia | 1.2–2 |
| Oxidation dyestuffs | Developing agents | 1 |
| | Coupling agents | 1 |
| Enzyme | Laccase | 0–5 |
| Water | | Balance |
| Component II: | Hydrogen peroxide dispersion | |
| Surfactants | Lauryl ether sulfate | 0.5–1 |
| Oxidants | Hydrogen peroxide | 6–9 |
| Stabilizers | 1-Hydroxyethane-1,1-diphosphonic acid | 1–1.5 |
| Thickeners | Polyacrylates | 3–5 |
| Enzyme | Laccase | 0–5 |
| Water | | Balance |

Shaving cream

| | | % |
|---|---|---|
| Soaps | Palmitic/Stearic acid | 30–40 |
| | Potassium hydroxide | 5–7 |
| | Sodium hydroxide | 1–2 |
| Fatty components | Coconut oil | 5–10 |
| | Polyethyleneglycol | 0–2 |
| Stabilizers | Sodium tetraborate | 0–0.5 |
| | Sodium silicate | 0–0.5 |
| | Sorbitol | 0–3 |
| Enzyme | Protease | 0–5 |
| Water | | Balance |

Shaving lotion

| | | % |
|---|---|---|
| Disinfecting and phonic acid | Ethanol | 40–80 |
| Refatting agents | Di-n-butyl adipate | 1–2 |
| Solubilizers | Ethoxylated castor oil | 0.5–1 |
| Adstringents | Vegetable extracts | 1–10 |
| Antiirritants | Panthenol | 0–0.5 |
| | Vegetable extracts | 0–2 |
| Stabilizers | Glycerine | 0–5 |
| | Sorbitol | 0–5 |
| | Propyleneglycol | 0–3 |
| Enzymes | Protease | 0–5 |
| Water | | Balance |

Hair pomade

| | | % |
|---|---|---|
| Consistency regulators | Fatty alcohols | 4–5 |
| | Ethoxylated lanolin alcohols | 3–6 |
| Mineral fats | Vaseline | 45–52 |
| | Branched chain paraffins | 10–18 |
| Antioxidants | 2,6-bis(1,1-Dimethylethyl)-4-methyl phenol (BHT) | 0.5–1 |
| Fragrances | | 0.2–0.4 |
| Dyestuffs | | 0.1 |
| Enzymes | Lipase | 0–5 |
| Emollients | Glycerine | Balance |

Setting lotion

| | | % |
|---|---|---|
| Solvents | Isopropanol | 12–20 |
| Film forming components | Vinyl pyrrolidone/vinyl acetate copolymers | 2–3.5 |
| Softening agents | Vinyl pyrrolidone/dimethyl amino ethyl methacrylate | 0.2–1 |
| Conditioners | Protein hydrolysates | 0.2–0.5 |
| Antistatics | Cetyl trimethyl ammonium chloride | 0.1–0.5 |

-continued

| Ingredients | Examples | |
|---|---|---|
| Emulsifiers | Etboxylated castor oil | 0.1–0.5 |
| Fragrances | | 0.1–0.2 |
| Dyestuffs | | <0.1 |
| Enzymes | Lipase | 0–5 |
| Water | | Balance |

In a final aspect the invention relates to the use of a modified enzyme of the invention for reducing the sensitisation potential of skin care products by reducing the IgE response when the skin care product is used.

Material and Methods

Materials

Enzymes:

PD498: Protease of subtilisin type shown in WO 93/24623. The sequence of PD498 is shown in SEQ ID NO. 1 and 2.

Subtilisin DY: Protease of the subtilisin type shown in SEQ ID NO. 4 isolated from Bacillus sp. variant (Detzel et al. (1993), Archives of Biophysics, Vol. 302, No. 2, p. 499–502).

ELISA Reagents:

Horse Radish Peroxidase labelled anti-rat-Ig (Dako, DK, P162, #031; dilution 1:1000).

Mouse anti-rat IgE (Serotec MCA193; dilution 1:200).

Rat anti-mouse IgE (Serotec MCA419; dilution 1:100).

Biotin-labelled mouse anti-rat IgG1 monoclonal antibody (Zymed 03-9140; dilution 1:1000)

Biotin-labelled rat anti-mouse IgG1 monoclonal antibody (Serotec MCA336B; dilution 1:1000)

Streptavidin-horse radish peroxidase (Kirkegard & Perry 14-30-00; dilution 1:1000).

Solutions:

Stop-solution (DMG-buffer)

Sodium Borate, borax (Sigma)

3,3-Dimethyl glutaric acid (Sigma)

$CaCl_2$ (Sigma)

Tresyl chloride (2,2,2-triflouroethansulfonyl chloride) (Fluka)

Tween 20: Poly oxyethylene sorbitan mono laurate (Merck cat no. 822184)

1-ethyl-3-(3-dimethylaminopropyl)carbodiimide (EDC) (Fluka)

N-Hydroxy succinimide (Fluka art. 56480))

Phosgene (Fluka art. 79380)

Lactose (Merck 7656)

PMSF (phenyl methyl sulfonyl flouride) from Sigma

Succinyl-Alanine-Alanine-Proline-Phenylalanine-para-nitroanilide(Suc-AAPF-pNP)Sigmano.

S-7388, Mw 624.6 g/mole.

Coloring Substrate:

OPD: o-phenylene-diamine, (Kementec cat no. 4260)

Test Animals:

Brown Norway rats (from Charles River, Del.)

The Brown Norway rats (BN) weighed at the starting time more than 250 grams and at termination approximately 450 grams.

Dunkin Hartley guinea pigs (from Charles River, Wiga Gmbh Sulzfeld 1, Sandhofer Weg, Del.).

Male Dunkin Hartley, which are sero negative for Parainfluenza 3, *E. cuniculi*, *K pneumonia* and *P multocida*. The animal weighed at the starting time 350–450 grams Female BALB/C mice (about 20 grams)(purchased from Bomholdtgaard, Ry, DK))

Equipment:
XCEL II (Novex)
ELISA reader (UVmax, Molecular Devices)
HPLC (Waters)
PFLC (Pharmacia)
Superdex-75 column, Mono-Q, Mono S from Pharmacia, SW.
SLT: Fotometer from SLT LabInstruments
Size-exclusion chromatograph (Spherogel TSK-G2000 SW).
Size-exclusion chromatograph (Superdex 200, Pharmacia, SW)
Amicon Cell Methods Immunization of BALB/C Mice Female Balb/C mice (20 grams) are immunized by subcutaneous injection of 50 µl of a 0.9% (wt./vol.) NaCl solution containing 25 µl of PD498, PD498-SPEG 5,000 and Glycine-SPEG-15,000 respectively. The amount of protein for each batch are measured by the Nanoorange Protein Quantification test (Molecular Probes Europe N-6666). Immunizations were performed every second week over a period of three months. Blood samples (200 µl) were collected from the eye one week after the immunization. Serum is obtained by blood clothing and centrifugation.

ELISA Procedure to Determine Relative Concentrations of IgG1 Antibodies in BALB/C Mice 1) Coat the ELIAS-plates with 1 µg protein/ml in coating buffer.

Incubate over night at 4° C., or at least 3 hours at room temperature. 50 µl/well. Shake gently.

2) Empty the plates and block with blocking buffer at least ½ hour at room temperature. 200 µl/well. Shake gently. Wash the plates 3 times with Washing Buffer.

3) Antigen is incubated with ½ dilutions of sera in Dilution Buffer. Make those solutions just before adding them to the wells. Keep some wells free for Dilution Buffer only (Blanks). Incubate at least 1 hour at room temperature. 50 µl/well. Shake gently. Wash the plates 3 times in Washing buffer.

4) Dilute biotin-labelled rat anti-mouse IgG1 monoclonal antibody or biotin-labelled mouse anti-rat IgG1 monoclonal antibody in Dilution Buffer. Incubate at room temperature at least 1 hour. 50 µl/well. Shake gently. Wash the plates 3 times in Washing Buffer.

5) Dilute Streptavidin-horse radish peroxidase in Dilution Buffer. Incubate at room temperature at least 1 hour. 50 µl/well. Shake gently. Wash the plates 3 times in Washing Buffer.

6) Mix 0.6 mg ODP/ml+0.4 µl $H_2O_2$/ml in substrate Buffer. Make the solution just before use. Incubate for 10 minutes. 50 µl/well.

7) To stop the reaction: add Stop Solution. 50 µl/well.

8) Read the plates at 492 nm with 620 nm as reference.

Data is calculated and presented in Lotus software.

ELISA Procedure to Determine Relative Concentrations of IgE Antibodies in BALB/C Mice A three layer sandwich ELISA is used to determine relative concentrations of specific IgE serum antibodies.

1) Coat the ELISA-plate with 10 µg rat anti-mouse IgE or mouse anti-rat IgE/ml buffer 1.

50 µl/well. Incubate over night at 4° C.

2) Empty the plates and block with Blocking buffer at least ½ hour at room temperature.

200 µl/well. Shake gently. Wash the plates 3 times with Washing Buffer.

Incubate with mouse/rat sera, starting from undiluted and continue with 2-fold dilutions. Keep some wells free for buffer 4 only (blanks). 50 µl/well. Incubate for 30 minutes at room temperature. Shake gently. Wash the plates 3 times in Washing Buffer.

4) Dilute the enzyme in Dilution buffer to the appropriate protein concentration. 50 µl/well.

Incubate for 30 minutes at room temperature. Shake gently. Wash the plates 3 times in Washing Buffer.

5) Dilute specific polyclonal anti-enzyme antiserum serum (pIg) for detecting bound antibody in Dilution buffer. 50 µl/well. Incubate for 30 minutes at room temperature. Shake gently. Wash the plates 3 times in Washing Buffer.

6) Dilute Horseradish Peroxidase-conjugated anti-pIg-antibody in Dilution buffer. 50 µl/well.

Incubate at room temperature for 30 minutes. Shake gently. Wash the plates 3 times in Washing Buffer.

7) Mix 0.6 mg ODP/ml+0.4 µl $H_2O_2$/ml in substrate Buffer. Make the solution just before use. Incubate for 10 minutes. 50 µl/well.

8) To stop the reaction: add Stop Solution. 50 µl/well.

9) Read the plates at 492 nm with 620 nm as reference.

Data is calculated and presented in Lotus.

ELISA Procedure for Determination of IgG1 Positive Guinea Pigs

ELISA microtiter plates are coated with rabbit anti-PD498 1:8000 in carbonate buffer (pH 9.6) and incubated over night at 4° C. The next day the plates is blocked with 2% BSA for 1 hour and washes 3 times with PBS Tween 20.

1 µg/ml PD498 is added to the plates and incubated for 1 hour, then washed 3 times with PBS Tween20.

All guinea pig sera samples and controls are applied to the ELISA plates with 2 µl sera and 98 µl PBS, incubated for 1 hour and washed 3 times with PBS Tween 20.

Then goat anti-guinea pig IgG1 (1:4000 in PBS buffer (Nordic Immunology 44–682)) is applied to the plates, incubated for 1 hour and washed with PBS tween 20.

Alkaline phosphatase marked rabbit anti-goat 1:8000 (Sigma A4187) is applied and incubated for 1 hour, washed 2 times in PBS Tween 20 and 1 time with diethanol amine buffer.

The marked alkaline phosphatase is developed using p-nitrophenyl phosphate for 30 minutes at 37° C. or until appropriate colour has developed.

The reaction is stopped using Stop medium ($K_2HPO_4$/$HaH_3$ buffer comprising EDTA (pH 10)) and read at OD 405/650 using a ELISA reader.

Double blinds are included on all ELISA plates.

Positive and negative sera values are calculated as the average blind values added 2 times the standard deviation. This gives an accuracy of 95%.

Intratracheal (IT) Stimulation of Rats

For IT administration of molecules disposable syringes with a 2½" long metal probe are used. This probe is instilled in the trachea of the rats approximately 1 cm below the epiglottis, and 0.1 ml of a solution of the molecules is deposited. The animals are stimulated 4 times, with 5 days between the last stimulation and exsanguination.

The test animals are Brown Norway rats (BN) in groups of 10. Weight at time of start is more than 250 grams and at termination approximately 450 grams.

Intratracheal (IT) Stimulation of Guinea Pigs For IT administration of molecules disposable syringes with a 2½" long metal probe are used. This probe is instilled in the trachea of the guinea pigs approximately 1 cm below the epiglottis, and 0.1 ml of a solution of the molecules is deposited. The animals are stimulated once a week for 10 consecutive weeks.

ELISA IgE Test System (for Brown Norway Rats)

A three layer sandwich ELISA is used to determine relative concentrations of specific antibodies.

The immunizing molecule is used as coating antigen with 10 μg per ml and 50 μl per well, in neutral phosphate buffer, incubated overnight at 4° C. All remaining binding spots on the well surface are blocked in 2% skim milk, 200 μl per well in phosphate buffer for at least 30 minutes at room temperature (RT). All seras to be tested with this antigen are added at 50 μl per well to this plate using a 8-channel pipette in dilution series from 10×diluted followed by 3-fold dilutions. Dilutions are made in phosphate buffer with 0.5% skim milk and 0.05% Tween20, incubated 2 hours on agitation platform at RT. The "tracer" molecule is biotinylated Mouse anti Rat IgE 50 μl per well and diluted 2000×in phosphate buffer with 0.5% skim milk and 0.05% Tween 20, incubated 2 hours on an agitation platform at RT. Control (blank) was identical sequence but without rat sera. 50 μl per well streptavidin horse raddish peroxidase, diluted 2000× was incubated 1 hour on an agitation platform. Colouring substrate at 50 μl per well is OPD (6 mg) and $H_2O_2$ (4 μl of a 30% solution) per 10 ml citrate buffer pH 5.2. The reaction is stopped using 100 μl per well 2 N $H_2SO_4$. All readings on SLT at 486 nm and 620 nm as reference. Data is calculated and presented in Lotus.

Determination of the Molecule Weight

Electrophoretic separation of proteins was performed by standard methods using 4–20% gradient SDS poly acrylamide gels (Novex). Proteins were detected by silver staining. The molecule weight was measured relative to the mobility of Mark-12® wide range molecule weight standards from Novex.

Protease Activity

Analysis with Suc-Ala-Ala-Pro-Phe-pNa:

Proteases cleave the bond between the peptide and p-nitroaniline to give a visible yellow colour absorbing at 405 nm.

Buffer: e.g. Britton and Robinson buffer pH 8.3 Substrate: 100 mg suc-AAPF-pNa is dissolved into 1 ml dimethyl sulfoxide (DMSO). 100 μl of this is diluted into 10 ml with Britton and Robinson buffer.

Analysis

The substrate and protease solution is mixed and the absorbance is monitored at 405 nm as a function of time and $ABS_{405\ nm}$/min. The temperature should be controlled (20–50° C. depending on protease). This is a measure of the protease activity in the sample.

EXAMPLES

Example 1

Activation of MPEG 15,000 with N-succinimidyl Carbonate mPEG 15,000 was suspended in toluene (4 ml/g of MPEG) 20% was distilled off at normal pressure to dry the reactants azeotropically. Dichloromethane (dry 1 ml/g MPEG) was added when the solution was cooled to 30° C. and phosgene in toluene (1.93 M 5 mole/mole MPEG) was added and mixture stirred at room temperature over night. The mixture was evaporated to dryness and the desired product was obtained as waxy lumps.

After evaporation dichloromethane and toluene (1:2, dry 3 ml/g mPEG) was added to re-dissolve the white solid. N-Hydroxy succinimide (2 mole/mole mPEG.) was added as a solid and then triethylamine (1.1 mole/mole MPEG). The mixture was stirred for 3 hours. initially unclear, then clear and ending with a small precipitate. The mixture was evaporated to dryness and recrystallised from ethyl acetate (10 ml) with warm filtration to remove salts and insoluble traces. The blank liquid was left for slow cooling at ambient temperature for 16 hours and then in the refrigerator over night. The white precipitate was filtered and washed with a little cold ethyl acetate and dried to yield 98% (w/w). NMR Indicating 80–90% activation and 5 o/oo (w/w) $HNEt_3Cl$. $^1H$-NMR for MPEG 15,000 ($CDCl_3$) δ1.42 t (I=4.8 $CH_3$ in $HNEt_3Cl$), 2.84 s (I=3.7 succinimide), 3.10 dq (I=3.4 $CH_2$ in $HNEt_3Cl$), 3.38 s (I=2.7 $CH_3$ in OMe), 3.40*dd (I=4.5 o/oo, $^{13}C$ satellite), 3.64 bs (I=1364 main peak), 3.89* dd (I=4.8 o/oo, $^{13}C$ satellite), 4.47 dd (I=1.8, $CH_2$ in PEG). No change was seen after storage in a desiccator at 22° C. for 4 months.

Example 2

Activation of mPEG 5.000 with N-succinimidyl Carbonate

Activation of MPEG 5,000 with N-succinimidyl carbonate was performed as described in Example 1.

Example 3

Conjugation of PD498 Protease with Activated MPEG 5,000

200 mg of PD498 was incubated in 50 mM NaBorate, pH 10, with 1.8 g of activated MPEG 5,000 with N-succinimidyl carbonate (prepared according to Example 2), in a final volume of 20 ml. The reaction was carried out at ambient temperature using magnetic stirring. Reaction time was 1 hour. The reaction was stopped by adding DMG buffer to a final concentration of 5 mM dimethyl glutarate, 1 mM $CaCl_2$ and 50 mM borate, pH 5.0.

The molecule weight of the obtained derivative was approximately 100 kDa, corresponding to about 13 moles of mPEG attached per mole PD498.

Compared to the parent enzyme, residual activity was close to 100% towards peptide substrate (succinyl-Ala-Ala-Pro-Phe-p-Nitroanilide).

Example 4

Conjugation of Subtilisin DY Protease with Activated MPEG 5,000

Subtilisin DY was conjugated to MPEG 5,000 with N-succinimidyl carbonate using the same procedure as described in Example 3.

Example 5

BALB/C Mice Subcutaneous (SC) Trails

BALB/C mice were stimulated subcutaneously (SC) with modified PD498-SPEG 5,000, parent unmodified PD498 and Glycine-SPEG 15,000 prepared as described in the examples above.

Sera from immunized mice were tested in a specific IgE ELISA (described above) to elucidate whether the molecules could activated the immune response system giving rise to a specific IgE response (See FIG. 1).

Four 2-weekly immunizations were sufficient to elicit an IgE response to PD498.

The 2-weekly immunization scheme was continued for 3 months. At the end of the study, seven immunizations were performed. As shown in FIG. 1, the anti-PD498 IgE levels in BALB/C mice with parent unmodified PD498 increased up to immunization #5, and stayed then rather constant. In contrast thereto, no specific IgE response was detected in mice immunized with modified PD498-SPEG 5,000.

Example 6

Allergenicity IT-trails of PD498-SPEG 5,000 in Guinea Pigs

Dunkin Hartley guinea pigs were stimulated with 1.0 μg purified PD498 and 1.0 μg modified PD498-SPEG 5,000 by intratracheal installation.

Figure 2:
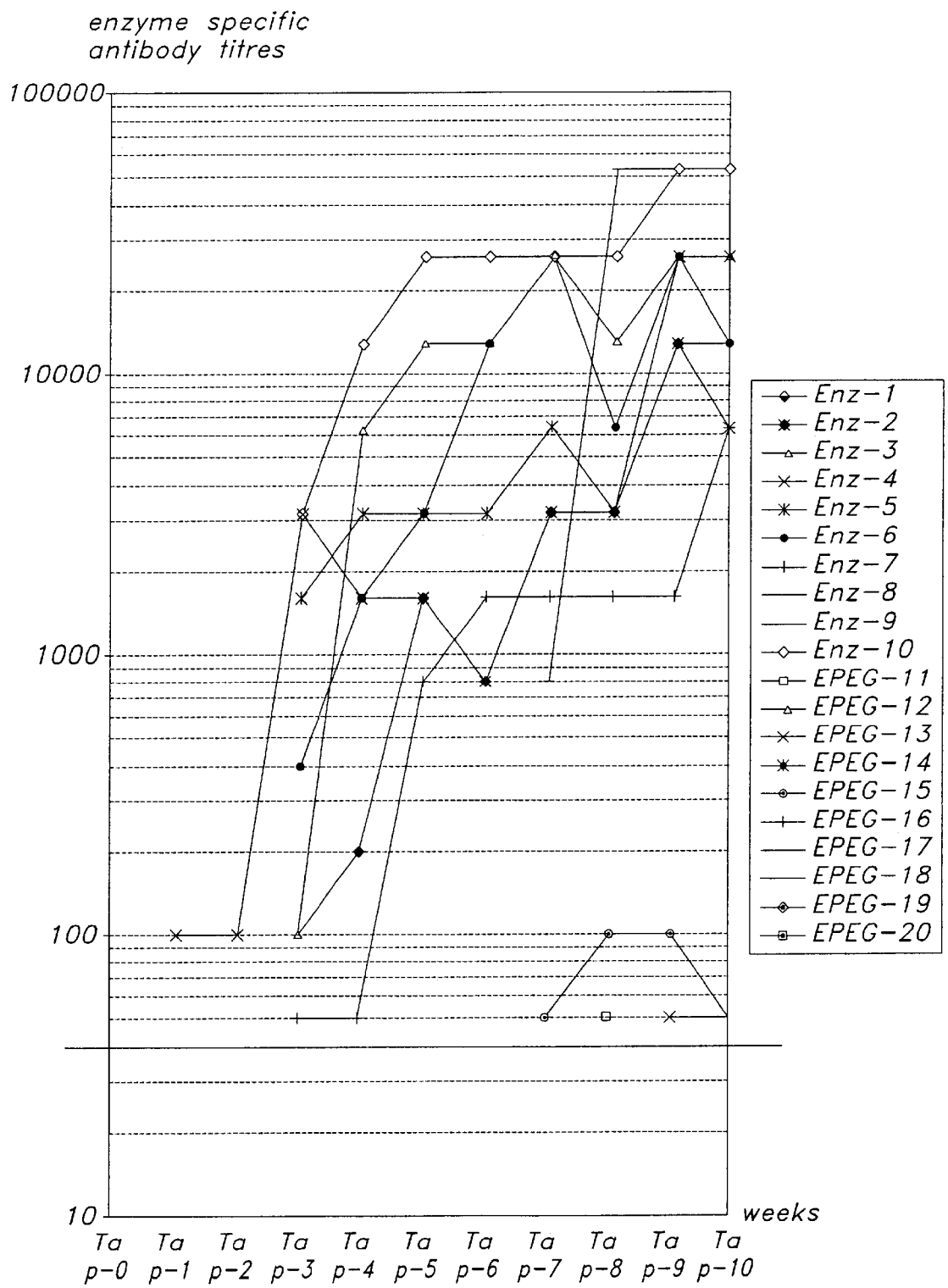
FIG. 2 shows the $IgG_1$ level of modified PD498-SPEG and unmodified PD498 of administrated intratrachaeally to Dunkin Hartley guinea pigs.

Sera from immunized Dunkin Hartley guinea pigs were tested during the trail period in a specific IgG$_1$ ELISA (described above) to elucidate whether the molecules could activated the immune response system giving rise to a specific IgG$_1$ response indicating an allergic response (See FIG. 2). The assay level was 1:50

FIG. 2 shows the IgG$_1$ levels of Dunkin Hartley guinea pigs during the trail period of 10 weeks. As can be seen the level of IgG$_1$ of the modified PD498 is not detectable before tapping no. #7 (Ta p-7) eqv. to 7 weeks. The IgG$_1$ level was not significantly increased upon successive stimulations with the modified PD498.

Example 7

Dose-response Intratrachaeal Trails (IT) in Guinea Pigs

The potential allergic response of modified PD498-SPEG 5,000 were tested in guinea pigs by IT trails. The guinea pigs were stimulated once a week for 10 consecutive weeks.

Before the first intratrachaeal stimulation a blood test was collected from each Dunkin Hartley guinea pig using the ELIAS for guinea pigs described above. This was done to make sure that there were no unspecific binding of sera in ELISA.

Groups of 10 guinea pigs were stimulated intratrachaeally (IT) with 0.3 micrograms, 3 micrograms, 30 micrograms, 300 micrograms of:

parent PD498, and modified PD498-SPEG 5,000.

The following solutions were used for blind tests 0.9% NaCl (Blind test for the parent PD498), and 300 micrograms PEG 5,000 in 0.9% NaCl corresponding to the amount of PEG in PD498-SPEG 5,000 (blind test for the modified PD498-SPEG).

Sera from all tested guinea pigs were tested in the IgG1 ELISA (described above). The result of the IT trails for the modified PD498-SPEG 5,000 are shown in FIG. 4. The result of the trails for the unmodified parent PD498 is shown in FIG. 3.

Figure 3:
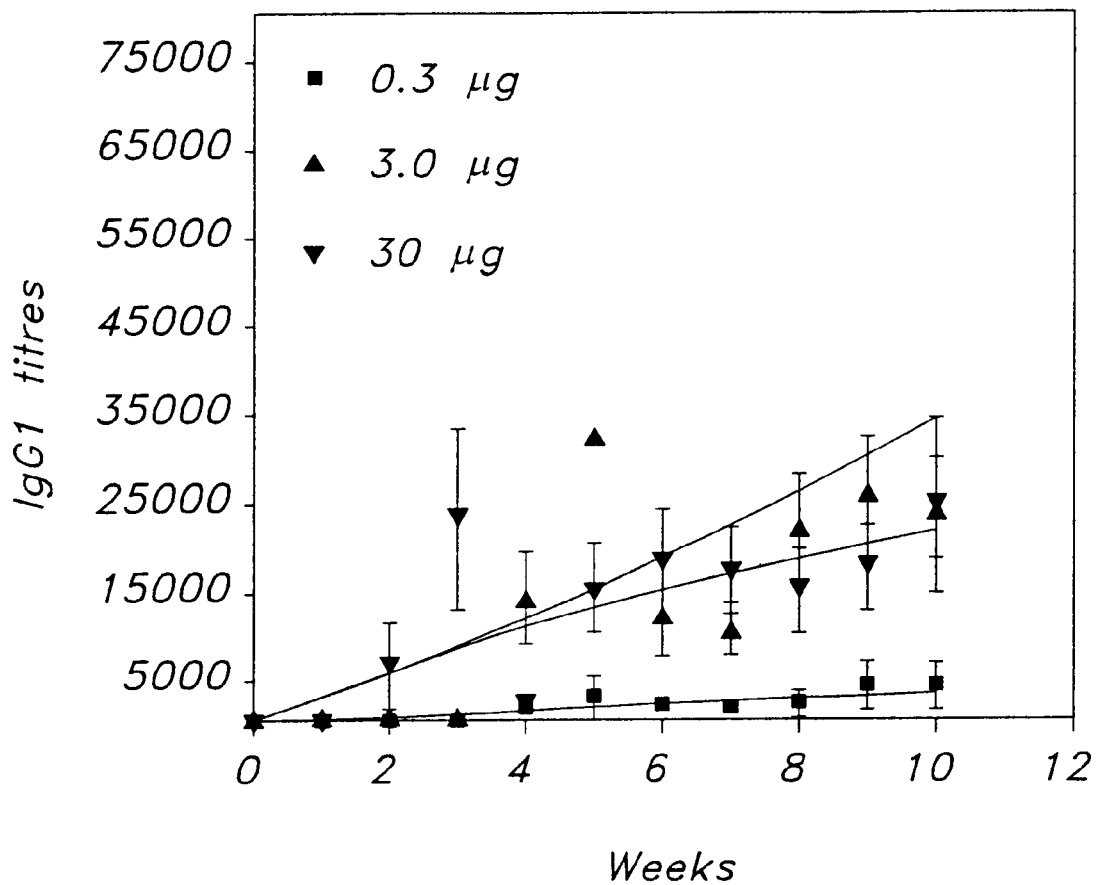
FIG. 3 shows the $IgG_1$ levels of 3 µg, 30 µg and 300 µg of modified PD498-SPEG 5,000 in the Dunkin Hartley guinea pigs IT dose response study (g 3.0 µg; s 30 µg; t 300 µg). The 0.3 µg dose curve is ommitted due to nor response at all.
Figure 4:
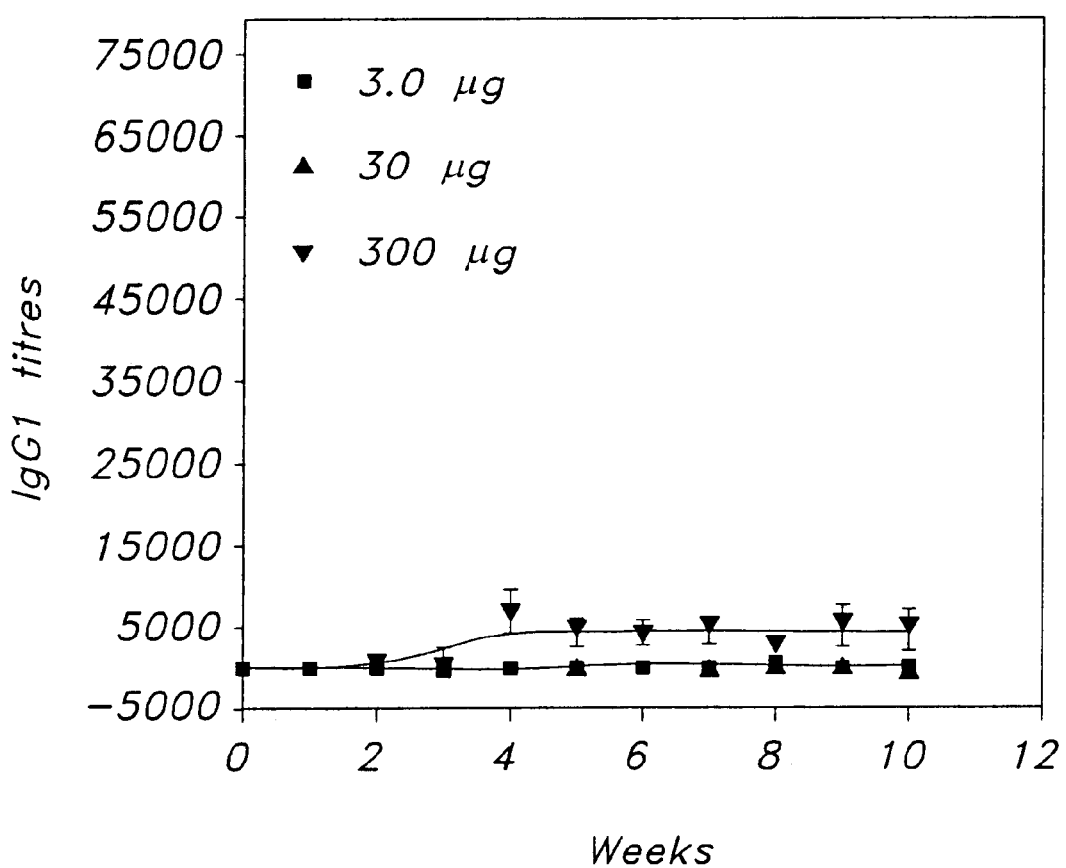
FIG. 4 shows the $IgG_1$ levels of 0.3 µg, 3.0 µg and 30 µg of unmodified parent PD498 in the Dunkin Hartley guinea pigs IT dose response study (g 0.3 µg; s 3.0 µg; t 30 µg).

As can be seen by comparing FIGS. 3 and 4 the response of the guinea pigs stimulated intratracheally with the modified enzyme is reduced in comparison to guinea pigs having been exposed intratracheally with the parent enzyme.

As will be apparent to those skilled in the art, in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A modified protease comprising a protease modified by having from 5 to 13 polymeric molecules, each molecule having a molecular weight of from 1 to 35 kDa, covalently coupled to the protease with or without a linker, wherein the protease has an amino acid sequence of SEQ ID NO: 2.

2. The modified protease of claim 1, wherein each polymeric molecule is a natural or synthetic homo- or heteropolymer.

3. The modified protease of claim 2, wherein each polymeric molecule is a polyalkylene glycol.

4. The modified protease of claim 2, wherein each polymeric molecule is (m)polyethylene glycol.

5. The modified protease of claim 2, wherein each polymeric molecule is polyethylene glycol.

6. The modified protease of claim 2, wherein each polymeric molecule is polypropylene glycol.

7. The modified protease of claim 2, wherein each polymeric molecule is selected from the group consisting of PEG-glycidyl ethers, PEG-oxycarbonylimidazole, branched PEGs, poly-vinyl alcohol (PVA), poly-carboxylates, poly-(vinylpyrolidone), poly-D,L-amino acids, polyethylene-co/maleic acid anhydride, and polystyrene-co-maleic acid anhydride.

8. The modified protease of claim 2, wherein each polymeric molecule is selected from the group consisting of dextrans, heparin, homologous albumin, celluloses, hydrolyzates of chitosan, starches, glycogen, agarose, guar gum, inulin, pullulan, xanthan gums, carrageenan, pectin and alginic acid hydrolyzates.

9. The modified protease of claim 1, wherein the protease is coupled to one or more of the following groups of the polymeric molecule: amino, hydroxyl, thiol, carboxyl, aldehyde or sulfydryl.

10. The modified protease of claim 1, wherein the polymeric molecules are coupled to the protease via a linker.

11. The modified protease of claim 10, wherein the linker is a triazine ring.

12. The modified protease of claim 9, wherein the polymeric molecules are coupled to the protease through an amino group.

13. The modified protease of claim 9, wherein the polymeric molecules are coupled to the protease at the N-terminal amino group and/or lysine residues.

14. The modified protease of claim 1, wherein the polymeric molecules are coupled to the protease at positions more than 5 Å from the active site of the protease.

15. The modified protease of claim 14, wherein the polymeric molecules are coupled to the protease more than 10 Å from the active site of the protease.

16. A skin care composition comprising a modified protease of claim 1 and further ingredients known to be used in skin care products.

17. A skin care product comprising a skin care composition of claim 16, wherein the product is selected from the group consisting of soap, cosmetics, skin creams, skin milk, skin lotion, skin gel, cleansing cream, cleansing lotion, cleansing milk, cold cream, cream soap, make-up base, milky lotion, pack, calamine lotion, T zone essence, hand cream, essence powder, whitening powder, powder soap, cake soap, transparent soap, lip cream, lipstick, nourishing essence, creamy foundation, face powder, powder eyeshadow, powder foundation, nail polish remover, hair tonic, hair liquid, hair cream, hair gel, hair setting preparations, hair dyes, hair colorants, shampoo, balsam, hair rinse, hair spray sun oil, sun screen, shaving foam, shaving cream, baby oil, acne care products, antiperspirants, Insect repellents, and deodorants.

* * * * *

SEQUENCE LISTING

<160> NUMBER OF SEQ ID NOS: 5

<210> SEQ ID NO 1
<211> LENGTH: 840
<212> TYPE: DNA
<213> ORGANISM: Bacillus sp. PD498, NCIMB No. 40484
<220> FEATURE:
<221> NAME/KEY: CDS
<222> LOCATION: (1)...(840)

<400> SEQUENCE: 1

```
tgg tca ccg aat gac cct tac tat tct gct tac cag tat gga cca caa      48
Trp Ser Pro Asn Asp Pro Tyr Tyr Ser Ala Tyr Gln Tyr Gly Pro Gln
 1               5                  10                  15 aac acc tca acc cct gct gcc tgg gat gta acc cgt gga agc agc act      96
Asn Thr Ser Thr Pro Ala Ala Trp Asp Val Thr Arg Gly Ser Ser Thr
             20                  25                  30 caa acg gtg gcg gtc ctt gat tcc gga gtg gat tat aac cac cct gat     144
Gln Thr Val Ala Val Leu Asp Ser Gly Val Asp Tyr Asn His Pro Asp
         35                  40                  45 ctt gca aga aaa gta ata aaa ggg tac gac ttt atc gac agg gac aat     192
Leu Ala Arg Lys Val Ile Lys Gly Tyr Asp Phe Ile Asp Arg Asp Asn
     50                  55                  60
```

```
aac cca atg gat ctt aac gga cat ggt acc cat gtt gcc ggt act gtt      240
Asn Pro Met Asp Leu Asn Gly His Gly Thr His Val Ala Gly Thr Val
 65              70                  75                  80 gct gct gat acg aac aat gga att ggc gta gcc ggt atg gca cca gat      288
Ala Ala Asp Thr Asn Asn Gly Ile Gly Val Ala Gly Met Ala Pro Asp
                     85                  90                  95 acg aag atc ctt gcc gta cgg gtc ctt gat gcc aat gga agt ggc tca      336
Thr Lys Ile Leu Ala Val Arg Val Leu Asp Ala Asn Gly Ser Gly Ser
                100                 105                 110 ctt gac agc att gcc tca ggt atc cgc tat gct gct gat caa ggg gca      384
Leu Asp Ser Ile Ala Ser Gly Ile Arg Tyr Ala Ala Asp Gln Gly Ala
            115                 120                 125 aag gta ctc aac ctc tcc ctt ggt tgc gaa tgc aac tcc aca act ctt      432
Lys Val Leu Asn Leu Ser Leu Gly Cys Glu Cys Asn Ser Thr Thr Leu
        130                 135                 140 aag agt gcc gtc gac tat gca tgg aac aaa gga gct gta gtc gtt gct      480
Lys Ser Ala Val Asp Tyr Ala Trp Asn Lys Gly Ala Val Val Val Ala
145                 150                 155                 160 gct gca ggg aat gac aat gta tcc cgt aca ttc caa cca gct tct tac      528
Ala Ala Gly Asn Asp Asn Val Ser Arg Thr Phe Gln Pro Ala Ser Tyr
                    165                 170                 175 cct aat gcc att gca gta ggt gcc att gac tcc aat gat cga aaa gca      576
Pro Asn Ala Ile Ala Val Gly Ala Ile Asp Ser Asn Asp Arg Lys Ala
                180                 185                 190 tca ttc tcc aat tac gga acg tgg gtg gat gtc act gct cca ggt gtg      624
Ser Phe Ser Asn Tyr Gly Thr Trp Val Asp Val Thr Ala Pro Gly Val
            195                 200                 205 aac ata gca tca acc gtt ccg aat aat ggc tac tcc tac atg tct ggt      672
Asn Ile Ala Ser Thr Val Pro Asn Asn Gly Tyr Ser Tyr Met Ser Gly
        210                 215                 220 acg tcc atg gca tcc cct cac gtg gcc ggt ttg gct gct ttg ttg gca      720
Thr Ser Met Ala Ser Pro His Val Ala Gly Leu Ala Ala Leu Leu Ala
225                 230                 235                 240 agt caa ggt aag aat aac gta caa atc cgc cag gcc att gag caa acc      768
Ser Gln Gly Lys Asn Asn Val Gln Ile Arg Gln Ala Ile Glu Gln Thr
                    245                 250                 255 gcc gat aag atc tct ggc act gga aca aac ttc aag tat ggt aaa atc      816
Ala Asp Lys Ile Ser Gly Thr Gly Thr Asn Phe Lys Tyr Gly Lys Ile
                260                 265                 270 aac tca aac aaa gct gta aga tac                                      840
Asn Ser Asn Lys Ala Val Arg Tyr
            275                 280

<210> SEQ ID NO 2
<211> LENGTH: 280
<212> TYPE: PRT
<213> ORGANISM: Bacillus sp. PD498, NCIMB No. 40484

<400> SEQUENCE: 2

Trp Ser Pro Asn Asp Pro Tyr Tyr Ser Ala Tyr Gln Tyr Gly Pro Gln
 1               5                  10                  15

Asn Thr Ser Thr Pro Ala Ala Trp Asp Val Thr Arg Gly Ser Ser Thr
                20                  25                  30

Gln Thr Val Ala Val Leu Asp Ser Gly Val Asp Tyr Asn His Pro Asp
            35                  40                  45

Leu Ala Arg Lys Val Ile Lys Gly Tyr Asp Phe Ile Asp Arg Asp Asn
        50                  55                  60

Asn Pro Met Asp Leu Asn Gly His Gly Thr His Val Ala Gly Thr Val
 65              70                  75                  80
```

```
Ala Ala Asp Thr Asn Asn Gly Ile Gly Val Ala Gly Met Ala Pro Asp
                85                  90                  95

Thr Lys Ile Leu Ala Val Arg Val Leu Asp Ala Asn Gly Ser Gly Ser
            100                 105                 110

Leu Asp Ser Ile Ala Ser Gly Ile Arg Tyr Ala Ala Asp Gln Gly Ala
            115                 120                 125

Lys Val Leu Asn Leu Ser Leu Gly Cys Glu Cys Asn Ser Thr Thr Leu
130                 135                 140

Lys Ser Ala Val Asp Tyr Ala Trp Asn Lys Gly Ala Val Val Val Ala
145                 150                 155                 160

Ala Ala Gly Asn Asp Asn Val Ser Arg Thr Phe Gln Pro Ala Ser Tyr
                165                 170                 175

Pro Asn Ala Ile Ala Val Gly Ala Ile Asp Ser Asn Asp Arg Lys Ala
                180                 185                 190

Ser Phe Ser Asn Tyr Gly Thr Trp Val Asp Val Thr Ala Pro Gly Val
                195                 200                 205

Asn Ile Ala Ser Thr Val Pro Asn Asn Gly Tyr Ser Tyr Met Ser Gly
                210                 215                 220

Thr Ser Met Ala Ser Pro His Val Ala Gly Leu Ala Ala Leu Leu Ala
225                 230                 235                 240

Ser Gln Gly Lys Asn Asn Val Gln Ile Arg Gln Ala Ile Glu Gln Thr
                245                 250                 255

Ala Asp Lys Ile Ser Gly Thr Gly Thr Asn Phe Lys Tyr Gly Lys Ile
                260                 265                 270

Asn Ser Asn Lys Ala Val Arg Tyr
                275                 280

<210> SEQ ID NO 3
<211> LENGTH: 274
<212> TYPE: PRT
<213> ORGANISM: Bacillus sp.
<220> FEATURE:
<221> NAME/KEY: VARIANT
<222> LOCATION: (0)...(0)
<223> OTHER INFORMATION: Xaa on position 37 is Ala or Ser
      Xaa on position 193 is Ala or Ser

<400> SEQUENCE: 3

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
                20                  25                  30

Thr Gly Ile Ala Xaa Ser His Thr Asp Leu Lys Val Val Gly Gly Ala
            35                  40                  45

Ser Phe Val Ser Gly Glu Ser Tyr Asn Thr Asp Gly Asn Gly His Gly
50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                85                  90                  95

Ser Ser Gly Ser Gly Thr Tyr Ser Ala Ile Val Ser Gly Ile Glu Trp
                100                 105                 110

Ala Thr Gln Asn Gly Leu Asp Val Ile Asn Met Ser Leu Gly Gly Pro
                115                 120                 125

Ser Gly Ser Thr Ala Leu Lys Gln Ala Val Asp Lys Ala Tyr Ala Ser
130                 135                 140
```

```
Gly Ile Val Val Ala Ala Gly Asn Ser Gly Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
            180                 185                 190

Xaa Glu Leu Glu Val Met Ala Pro Gly Val Ser Val Tyr Ser Thr Tyr
        195                 200                 205

Pro Ser Asn Thr Tyr Thr Ser Leu Asn Gly Thr Ser Met Ala Ser Pro
    210                 215                 220

His Val Ala Gly Ala Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
                245                 250                 255

Gly Asp Ser Phe Tyr Tyr Gly Lys Gly Leu Ile Asn Val Glu Ala Ala
            260                 265                 270

Ala Gln

<210> SEQ ID NO 4
<211> LENGTH: 433
<212> TYPE: PRT
<213> ORGANISM: Bacillus sp.

<400> SEQUENCE: 4

Asn Asp Val Ala Arg Gly Ile Val Lys Ala Asp Val Ala Gln Asn Asn
1               5                   10                  15

Tyr Gly Leu Tyr Gly Gln Gly Gln Leu Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Ser Asp
        50                  55                  60

Pro Asn Gly His Gly Thr His Val Ala Gly Ser Val Leu Gly Asn Ala
65                  70                  75                  80

Leu Asn Lys Gly Met Ala Pro Gln Ala Asn Leu Val Phe Gln Ser Ile
                85                  90                  95

Met Asp Ser Ser Gly Gly Leu Gly Gly Leu Pro Ser Asn Leu Asn Thr
            100                 105                 110

Leu Phe Ser Gln Ala Trp Asn Ala Gly Ala Arg Ile His Thr Asn Ser
        115                 120                 125

Trp Gly Ala Pro Val Asn Gly Ala Tyr Thr Ala Asn Ser Arg Gln Val
    130                 135                 140

Asp Glu Tyr Val Arg Asn Asn Asp Met Thr Val Leu Phe Ala Ala Gly
145                 150                 155                 160

Asn Glu Gly Pro Asn Ser Gly Thr Ile Ser Ala Pro Gly Thr Ala Lys
                165                 170                 175

Asn Ala Ile Thr Val Gly Ala Thr Glu Asn Tyr Arg Pro Ser Phe Gly
            180                 185                 190

Ser Ile Ala Asp Asn Pro Asn His Ile Ala Gln Phe Ser Ser Arg Gly
        195                 200                 205

Ala Thr Arg Asp Gly Arg Ile Lys Pro Asp Val Thr Ala Pro Gly Thr
    210                 215                 220

Phe Ile Leu Ser Ala Arg Ser Ser Leu Ala Pro Asp Ser Ser Phe Trp
225                 230                 235                 240
```

```
Ala Asn Tyr Asn Ser Lys Tyr Ala Tyr Met Gly Gly Thr Ser Met Ala
                245                 250                 255

Thr Pro Ile Val Ala Gly Asn Val Ala Gln Leu Arg Glu His Phe Ile
            260                 265                 270

Lys Asn Arg Gly Ile Thr Pro Lys Pro Ser Leu Ile Lys Ala Ala Leu
        275                 280                 285

Ile Ala Gly Ala Thr Asp Val Gly Leu Gly Tyr Pro Ser Gly Asp Gln
    290                 295                 300

Gly Trp Gly Arg Val Thr Leu Asp Lys Ser Leu Asn Val Ala Tyr Val
305                 310                 315                 320

Asn Glu Ala Thr Ala Leu Ala Thr Gly Gln Lys Ala Thr Tyr Ser Phe
                325                 330                 335

Gln Ala Gln Ala Gly Lys Pro Leu Lys Ile Ser Leu Val Trp Thr Asp
            340                 345                 350

Ala Pro Gly Ser Thr Thr Ala Ser Tyr Thr Leu Val Asn Asp Leu Asp
        355                 360                 365

Leu Val Ile Thr Ala Pro Asn Gly Gln Lys Tyr Val Gly Asn Asp Phe
    370                 375                 380

Ser Tyr Pro Tyr Asp Asn Asn Trp Asp Gly Arg Asn Asn Val Glu Asn
385                 390                 395                 400

Val Phe Ile Asn Ala Pro Gln Ser Gly Thr Tyr Ile Ile Glu Val Gln
                405                 410                 415

Ala Tyr Asn Val Pro Ser Gly Pro Gln Arg Phe Ser Leu Ala Ile Val
            420                 425                 430

His

<210> SEQ ID NO 5
<211> LENGTH: 316
<212> TYPE: PRT
<213> ORGANISM: Bacillus thermoproteolyticus

<400> SEQUENCE: 5

Ile Thr Gly Thr Ser Thr Val Gly Val Gly Arg Gly Val Leu Gly Asp
  1               5                  10                  15

Gln Lys Asn Ile Asn Thr Thr Tyr Ser Thr Tyr Tyr Tyr Leu Gln Asp
                 20                  25                  30

Asn Thr Arg Gly Asp Gly Ile Phe Thr Tyr Asp Ala Lys Tyr Arg Thr
             35                  40                  45

Thr Leu Pro Gly Ser Leu Trp Ala Asp Ala Asp Asn Gln Phe Phe Ala
         50                  55                  60

Ser Tyr Asp Ala Pro Ala Val Asp Ala His Tyr Tyr Ala Gly Val Thr
 65                  70                  75                  80

Tyr Asp Tyr Tyr Lys Asn Val His Asn Arg Leu Ser Tyr Asp Gly Asn
                 85                  90                  95

Asn Ala Ala Ile Arg Ser Ser Val His Tyr Ser Gln Gly Tyr Asn Asn
             100                 105                 110

Ala Phe Trp Asn Gly Ser Glu Met Val Tyr Gly Asp Gly Asp Gly Gln
         115                 120                 125

Thr Phe Ile Pro Leu Ser Gly Gly Ile Asp Val Val Ala His Glu Leu
     130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
                165                 170                 175
```

-continued

```
Glu Phe Tyr Ala Asn Lys Asn Pro Asp Trp Glu Ile Gly Glu Asp Val
            180                 185             190

Tyr Thr Pro Gly Ile Ser Gly Asp Ser Leu Arg Ser Met Ser Asp Pro
        195             200                 205

Ala Lys Tyr Gly Asp Pro Asp His Tyr Ser Lys Arg Tyr Thr Gly Thr
    210             215             220

Gln Asp Asn Gly Gly Val His Ile Asn Ser Gly Ile Ile Asn Lys Ala
225             230             235                     240

Ala Tyr Leu Ile Ser Gln Gly Gly Thr His Tyr Gly Val Ser Val Val
            245             250                 255

Gly Ile Gly Arg Asp Lys Leu Gly Lys Ile Phe Tyr Arg Ala Leu Thr
            260             265             270

Gln Tyr Leu Thr Pro Thr Ser Asn Phe Ser Gln Leu Arg Ala Ala Ala
        275             280                 285

Val Gln Ser Ala Thr Asp Leu Tyr Gly Ser Thr Ser Gln Glu Val Ala
        290             295             300

Ser Val Lys Gln Ala Phe Asp Ala Val Gly Val Lys
305             310             315
```